United States Patent [19]

Suh et al.

[11] 4,022,910

[45] * May 10, 1977

[54] L-3-HYDROXYMETHYLTYROSINE AND SALTS THEREOF FOR LOWERING BLOOD PRESSURE

[75] Inventors: John T. Suh, Mequon, Wis.; Richard A. Schnettler, Cincinnati, Ohio

[73] Assignee: Richardson-Merrell Inc., Wilton, Conn.

[ * ] Notice: The portion of the term of this patent subsequent to July 23, 1991, has been disclaimed.

[22] Filed: Feb. 9, 1976

[21] Appl. No.: 656,103

Related U.S. Application Data

[60] Continuation-in-part of Ser. No. 501,980, Aug. 30, 1974, abandoned, which is a division of Ser. No. 317,800, Dec. 22, 1972, Pat. No. 3,904,680.

[52] U.S. Cl. .............................................. 424/319
[51] Int. Cl.$^2$ .................................... A61K 31/195
[58] Field of Search .................................... 424/319

[56] References Cited

UNITED STATES PATENTS

| | | | |
|---|---|---|---|
| 3,592,844 | 7/1971 | Reinhold | 260/519 |
| 3,825,590 | 7/1974 | Suh et al. | 260/519 |

*Primary Examiner*—Stanley J. Friedman
*Attorney, Agent, or Firm*—L. Ruth Hattan; Eugene O. Retter; George W. Rauchfuss, Jr.

[57] ABSTRACT

L-3-Hydroxymethyltyrosine and pharmaceutically acceptable salts thereof useful in lowering blood pressure and compositions thereof.

4 Claims, No Drawings

L-3-HYDROXYMETHYLTYROSINE AND SALTS THEREOF FOR LOWERING BLOOD PRESSURE

This is a continuation-in-part of application Ser. No. 501,980 filed Aug. 30, 1974, now abandoned, which is a divisional of Ser. No. 317,800, filed Dec. 22, 1972, now U.S. Pat. No. 3,904,680 issued Sept. 9, 1975.

RELATED CASE

In U.S. Pat. No. 3,825,590 issued July 23, 1974, the DL form of 3-hydroxymethyltyrosine is disclosed.

BACKGROUND OF THE INVENTION

The compound 3-formyltyrosine is disclosed in German Offenlegungsschrift No. 2,122,485.

SUMMARY OF THE INVENTION

The compound L-3-hydroxymethyltyrosine may be represented by the following formula:

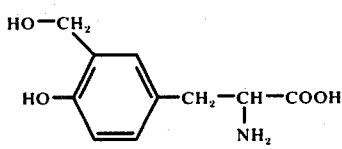

The preferred method of preparing L-3-hydroxymethyltyrosine comprises heating an aqueous mixture of L-tyrosine to about 90° C., adding acetic anhydride to the mixture with stirring, and then concentrating the mixture to dryness. The resulting amide is dissolved in aqueous sodium hydroxide, and dimethyl sulfate is added to form L-0-methyl-N-acetyltyrosine which is dissolved in an ethyl alcohol-chloroform solution, treated with p-toluenesulfonic acid and heated at reflux to form the corresponding ethyl ester. The ethyl ester is then dissolved in methylene chloride, titanium tetrachloride and the solution chilled. To the chilled solution is added α,α-dichloromethyl methyl ether to form L-4-methoxy-3-formyl-N-acetyltyrosine ethyl ester. The thus obtained ethyl ester is reacted with a solution of boron trichloride in methylene chloride to form L-3-formyl-N-acetyltyrosine ethyl ester which upon treatment with 4 N hydrochloric acid forms L-3-formyltyrosine hydrochloride. The resulting compound is then treated with potassium carbonate to form the free base 3-formyltyrosine, which is dissolved in water and hydrogenated at 40 psi of hydrogen in the presence of a platinum oxide catalyst to form L-3-hydroxymethyltyrosine.

The process may be illustrated as follows:

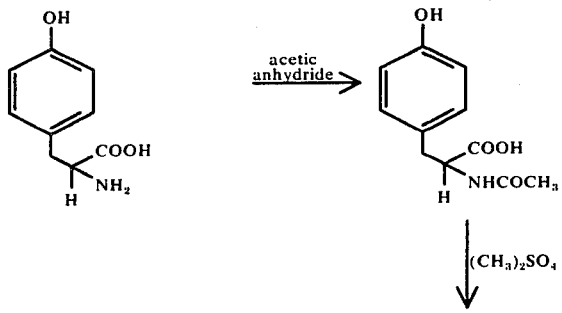

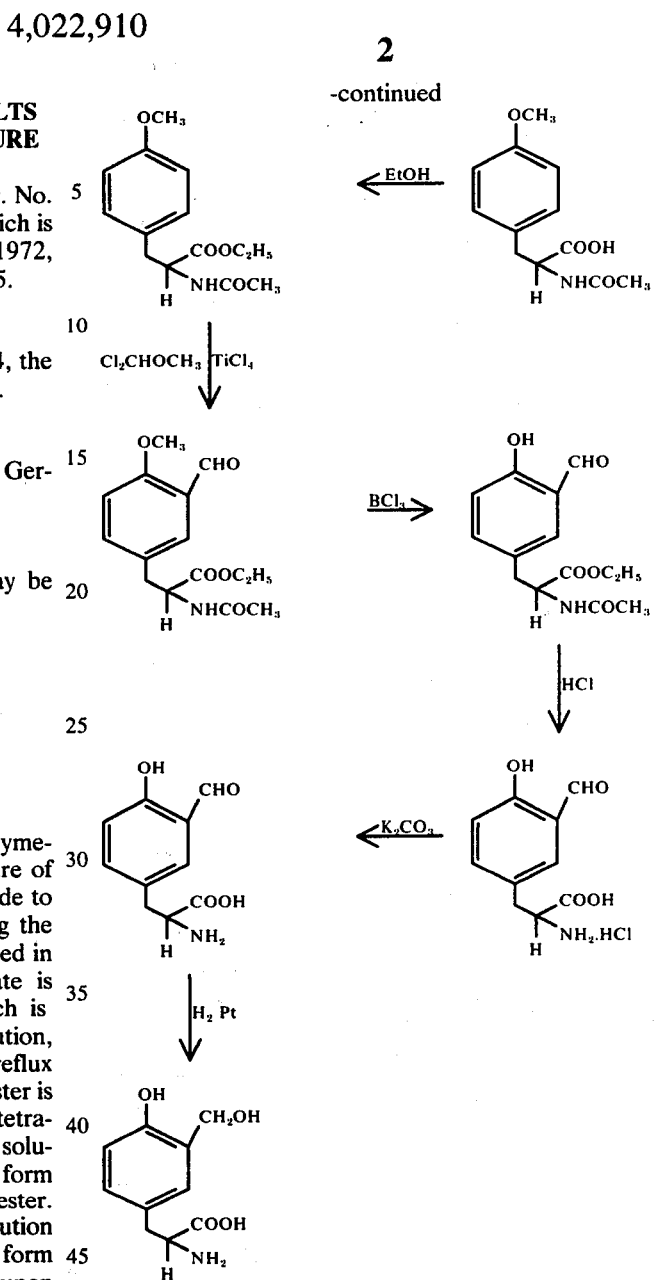

The compound of the present invention may be employed as a chelating agent in chemical processes in which it is desirable to inactivate heavy metal ions, especially ferric ions. The compound can simply be dissolved in warm water and added to the aqueous mixture containing the heavy metal ions in an amount calculated to be sufficient to inactivate the ions. In addition, the compound L-3-hydroxymethyltyrosine possesses antihypertensive activity rendering it useful in lowering blood pressure.

Pharmaceutically acceptable salts of the novel compounds may be prepared by reacting the amino acid in a suitable mutual solvent with an acid such as formic acid, citric acid, maleic acid, sulfuric acid, hydrochloric acid, succinic acid, tartaric acid, benzoic acid and fumaric acid.

When employed as pharmaceutical agents, the novel amino acids are preferably combined with conventional pharmaceutical diluents, flavoring agents, disintegrating and lubricant ingredients and formed into conventional oral unit dosage forms such as capsules, tablets and the like, and parenteral dosage forms such as solutions.

The number of tablets or capsules an individual patient may receive in a given 24 hour period will, of course, depend upon the amount of medication contained in the unit dosage form selected and the patient's condition.

The compounds of this invention can be administered orally or parenterally either alone or in the form of pharmaceutical preparations, to a patient, such as, animals, mammals, rats, mice, cats, dogs, bovine cows, horses, sheep and humans. Pharmaceutical preparations containing conventional pharmaceutical carriers and as active ingredients compounds of this invention can be employed in unit dosage forms such as solids, for example, tablets, capsules, and pills, or liquid solutions, suspensions, or emulsions for oral and parenteral administration. The dosage unit administered can be any amount effective as an antihypertensive. The quantity of compound administered can vary over a wide range to provide from about 5.0 mg/kg (milligram per kilogram) to about 300 mg/kg of body weight of the patient per day, and preferably, from about 10 mg/kg to 30 mg/kg of body weight of the patient per day, to achieve the desired effect. Unit doses can contain from about 10 mg to 500 mg of a compound of this invention and may be administered, for example, from 1 to 4 times daily.

The following examples illustrate the practice of the invention:

EXAMPLE 1

L-O-Methyl-N-acetyltyrosine

To a suspension of 45 g (0.25 mole) tyrosine in 500 ml water heated to 90° C. is added 190 ml acetic anhydride dropwise over a 15 minute period. The heat is removed during the addition of the acetic anhydride. The solution is stirred an additional 15 minutes and concentrated to dryness. The residue is dissolved in 140 ml water containing 30 g sodium hydroxide. To the solution is slowly added 41 ml. dimethyl sulfate over a 30 minute period. Toward the end of the addition, 40 ml 10% sodium hydroxide is added to maintain basicity of the solution. The solution is stirred an additional 30 minutes, cooled, and acidified with concentrated hydrochloric acid. A gum which forms is extracted with chloroform. The organic solution is washed with water and dried and filtered. The chloroform phase is concentrated to 250 ml and refrigerated. The white solid which crystallizes has a m.p. of 142°-145° C.

EXAMPLE 2

L-O-Methyl-N-acetyltyrosine ethyl ester

A solution of 15 g (0.063 mole) L-O-methyl-N-acetyltyrosine in 100 ml ethanol and 400 ml chloroform is charged with 1.0 g p-toluenesulfonic acid and refluxed 15 hours, poured into H₂O, extracted with chloroform, washed with water and dried. Evaporation of solvent affords L-O-methyl-N-acetyltyrosine ethyl ester as a solid, m.p. 85°-90° C.

EXAMPLE 3

L-4-Methoxy-3-formyl-N-acetyltyrosine ethyl ester

To a chilled solution of b 17.8 g (0.067 mole) L-O-methyl-N-acetyltyrosine ethyl ester in 300 ml methylene chloride is added dropwise 50 ml titanium tetrachloride. A deep orange solution is obtained. To the chilled solution is added 20 ml $\alpha,\alpha$-dichloromethyl methyl ether over a 10 minute period. The solution is allowed to warm to room temperature and is stirred for 2 hours. The mixture is poured into 200 g ice and 200 ml 3N HCl and extracted with methylene chloride, washed with water and dried. Evaporation of solvent gives a semi-solid which on chromatography over silica gel gives purified L-4-methoxy-3-formyl-N-acetyltyrosine ethyl ester, m.p. 85° C.

EXAMPLE 4

L-3-Formyl-N-acetyltyrosine ethyl ester

In 200 ml cold methylene chloride is dissolved 29 g boron trichloride to which is added 7.0 g (0.0239 mole) L-4-methoxy-3-formyl-N-acetyltyrosine ethyl ester. The solution is stirred 15 hours at room temperature during which time a green gum is deposited on the flask. Water (1000 ml) is added dropwise to the reaction mixture. The organic layer is separated, washed with water, and dried. Evaporation of solvent gives a pink oil which is chromatographed over silica gel to give L-3-formyl-N-acetyltyrosine ethyl ester as a crystalline solid, m.p. 116° C.

EXAMPLE 5

L-3-Formyltyrosine hydrochloride

In 20 ml 4N hydrochloric acid is suspended 1.67 g L-3-formyl-N-acetyltyrosine ethyl ester. The mixture is refluxed one hour and the solvent evaporated to give a pink solid which is triturated with isopropanol:ether to give L-3-formyltyrosine hydrochloride as a solid.

EXAMPLE 6

L-3-Hydroxymethyltyrosine

In 40 ml water is dissolved 3.4204 g (0.0139 mole) L-3-formyltyrosine hydrochloride. Potassium carbonate (0.965 g, 0.00697 mole) is added and the solution allowed to stand 15 hours. Yellow crystals of 3-formyltyrosine are obtained, collected and rinsed with 10 ml cold water and 10 ml isopropanol. The material is dried to give 2.28 g (78%) yellow solid. The free amino acid is dissolved in 250 ml water and hydrogenated over 0.3 g platinum oxide at 40 psi hydrogen. After 1.5 hours the theoretical volume of hydrogen is absorbed. After filtering and concentrating the solvent to 20 ml, a white precipitate forms which is removed by filtration. The fitrate is allowed to evaporate to dryness and redissolved in 20 ml water. The insoluble factor is again removed and the filtrate allowed to evaporate to dryness. Trituration with ethanol afford L-3-hydroxymethyltyrosine as a white solid which does not melt at 360°: $[\alpha]_D^{25} = -30.49°$.

Anal. Calcd. for $C_{10}H_{13}NO_4$: C, 56.86; H, 6.20; N, 6.63. Found: C, 56.93; H, 6.24; N, 6.54.

EXAMPLE 7

An illustrative composition for tablets is as follows:

|     |                          | Per Tablet |
| --- | ------------------------ | ---------- |
| (a) | L-3-hydroxymethyltyrosine | 100.0 mg |
| (b) | wheat starch             | 15.0 mg    |
| (c) | lactose                  | 33.5 mg    |
| (d) | magnesium stearate       | 1.5 mg     |

A portion of the wheat starch is used to make a granulated starch paste which together with the remainder of the wheat starch and the lactose is granulated, screened and mixed with the active ingredient (a), and the magnesium stearate. The mixture is compressed into tablets weighing 150 mg each.

EXAMPLE 8

An illustrative composition for hard gelatin capsules is as follows:

|     |                          | Amount   |
| --- | ------------------------ | -------- |
| (a) | L-3-hydroxymethyltyrosine | 200.0 mg |
| (b) | talc                     | 35.0 mg  |

The composition is prepared by passing the dry powders of (a) and (b) through a fine mesh screen and mixing them well. The powder is then filled into No. 0 hard gelatin capsules at a net fill of 235 mg per capsule.

EXAMPLE 9

An illustrative composition for a parenteral injection is the following wherein the quantities are on a weight to volume basis.

|     |                              | Amount  |
| --- | ---------------------------- | ------- |
| (a) | L-3-hydroxymethyltyrosine    | 100.0 g |
| (b) | sodium chloride              | q.s.    |
| (c) | water for injection to make  | 20 ml   |

The composition is prepared by dissolving the active ingredient (a) and sufficient sodium chloride in water for injection to render the solution isotonic. The composition may be dispensed in a single ampule containing 100 mg of the active ingredient for multiple dosage or in 20 ampules for single dosage.

We claim:

1. A pharmaceutical composition comprising a blood-pressure lowering effective amount of a compound selected from the group consisting of L-3-hydroxymethyltyrosine or a pharmaceutically acceptable salt thereof in combination with a pharmaceutical diluent.

2. A composition of claim 1 wherein the compound is L-3-hydroxymethyltyrosine.

3. A method of lowering blood pressure in a patient which comprises administering to said patient a blood-pressure lowering effective amount of a compound selected from the group consisting of L-3-hydroxymethyltyrosine or a pharmaceutically acceptable salt thereof.

4. A method of claim 3 wherein the compound is L-3-hydroxymethyltyrosine.

* * * * *